US00PP37018P2

(12) United States Plant Patent
Farrow

(10) Patent No.: US PP37,018 P2
(45) Date of Patent: Oct. 14, 2025

(54) ***ILEX* PLANT NAMED 'FARROWICUPRT'**

(50) Latin Name: *Ilex crenata*
Varietal Denomination: FARROWICUPRT

(71) Applicant: Spring Meadow Nursery, Grand Havem, MI (US)

(72) Inventor: Michael W. Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/018,067

(22) Filed: Jan. 13, 2025

(51) Int. Cl.
*A01H 5/00* (2018.01)
*A01H 6/00* (2018.01)

(52) U.S. Cl.
USPC ..... Plt./247

(58) Field of Classification Search
USPC ..... Plt./226, 247
See application file for complete search history.

*Primary Examiner* — Susan McCormick Ewoldt
(74) *Attorney, Agent, or Firm* — Cassandra Bright

(57) ABSTRACT

A new and distinct cultivar of *Ilex* plant named 'FARROWICUPRT' is disclosed, characterized by attractive dark green foliage, extending the base of the plant. Plants have upright habits with dense, tidy branching. Plants are female and fruit-bearing. The new cultivar is an *Ilex*, suitable for ornamental garden purposes.

3 Drawing Sheets

Latin name of the genus and species: *Ilex crenata.*
Cultivar denomination: 'FARROWICUPRT'.

BACKGROUND OF THE INVENTION

The new cultivar is a product of a planned breeding program by the inventor, to develop new and interesting *Ilex* varieties. The open-pollination resulting in the new cultivar was made during the spring of 2014, at a nursery in Warwick, Maryland. The seed parent is the unpatented cultivar *Ilex* 'Sky Pencil'. The pollen parent is unidentified. The inventor discovered this new cultivar at the same nursery during the fall of 2014.

After identifying the new cultivar as a potentially interesting selection, the inventor first asexually propagated plants of 'FARROWICUPRT' by stem cuttings during the summer of 2016 at the same nursery in Warwick, Maryland. Multiple generations have been reproduced and have shown that the unique features of this cultivar are stable and reproduced true to type.

SUMMARY OF THE INVENTION

The cultivar 'FARROWICUPRT' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWICUPRT' These characteristics in combination distinguish 'FARROWICUPRT' as a new and distinct *Ilex* cultivar:

1. Upright, columnar/fastigiate habit.
2. Attractive, dark green foliage that maintains its color year-round.
3. Dense, tidy branching without gaps.

4. Foliage which extends to the base of the plant, nearly touching the ground.
5. Female; fruit bearing.

COMPARISON TO PARENT CULTIVAR

'FARROWICUPRT' is similar in most horticultural characteristics to the seed parent cultivar 'Sky Pencil'. Plants of the new cultivar 'FARROWICUPRT' however, differ in the following:

1. Plants of the new cultivar are approximately 30% broader in habit than plants of the seed parent.
2. Internodes of the new cultivar are 10% to 50% the size of internodes of the seed parent, forming a denser plant without gaps.

COMMERCIAL COMPARISON

'FARROWICUPRT' can be compared to the commercial cultivar *Ilex crenata* 'Farrowone', U.S. Plant Pat. No. 20,049. Plants of the new cultivar 'FARROWICUPRT' are similar to plants of 'Farrowone' in most horticultural characteristics, however, plants of the new cultivar 'FARROWICUPRT' differ in the following:

1. Plants of the new cultivar have a denser, tighter branching habit, than plants of this comparator.
2. New growth of the new cultivar all grows in the same, upward direction, lending to a tidier appearance. New growth of this comparator extends both upward and outward, making the plant appear less tidy overall.

BRIEF DESCRIPTION OF THE PHOTOGRAPHS

The accompanying photograph in FIG. 1 illustrates in full color a plant of 'FARROWICUPRT' grown in a poly-greenhouse in Warwick, MD at about 7 years of age in a 7-gallon pot.

DETAILED BOTANICAL DESCRIPTION

Figure 1:
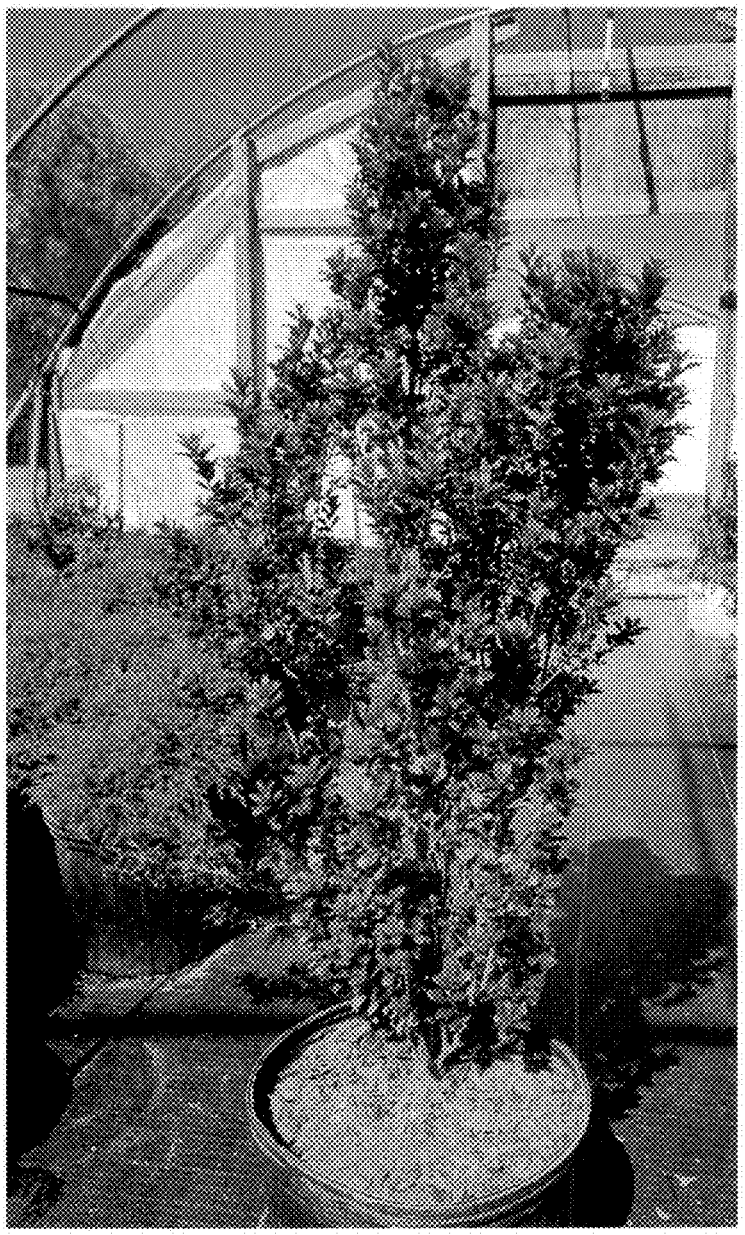
Figure 2:
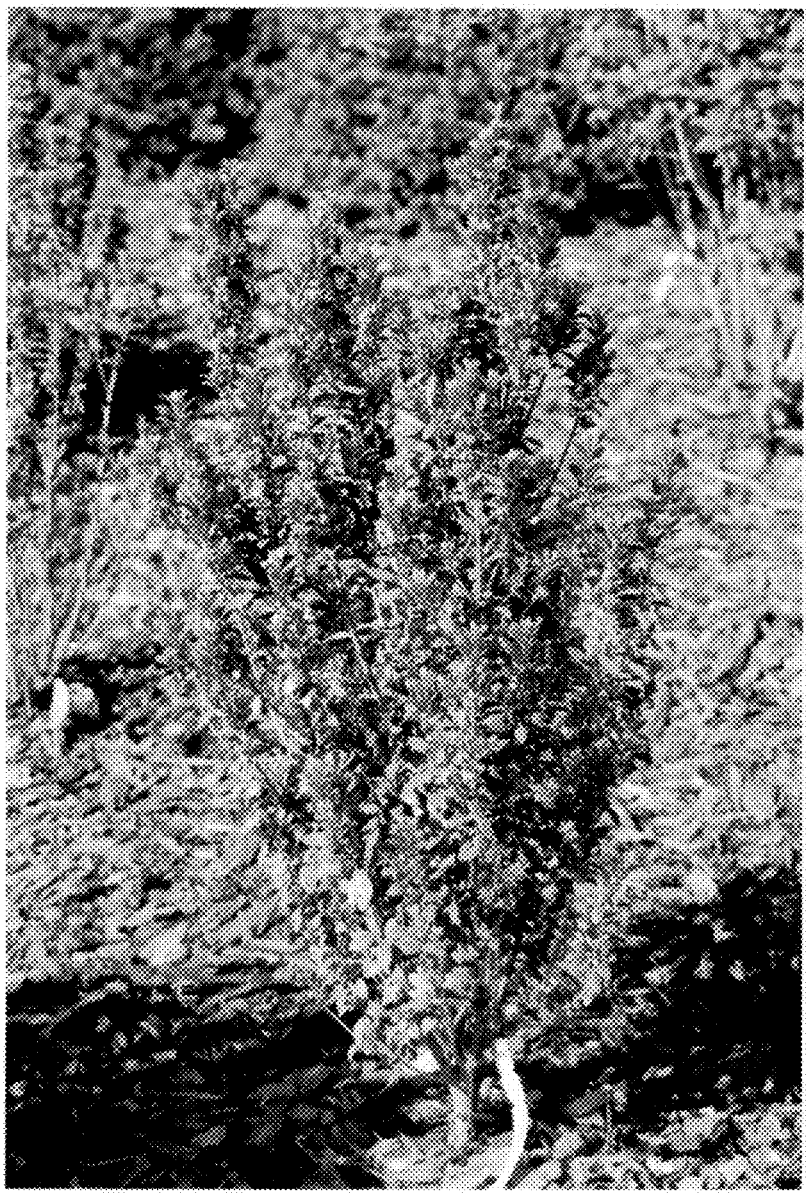
FIG. 2 shows a field grown plant of 'FARROWICUPRT' at about 2 years of age.
Figure 3:
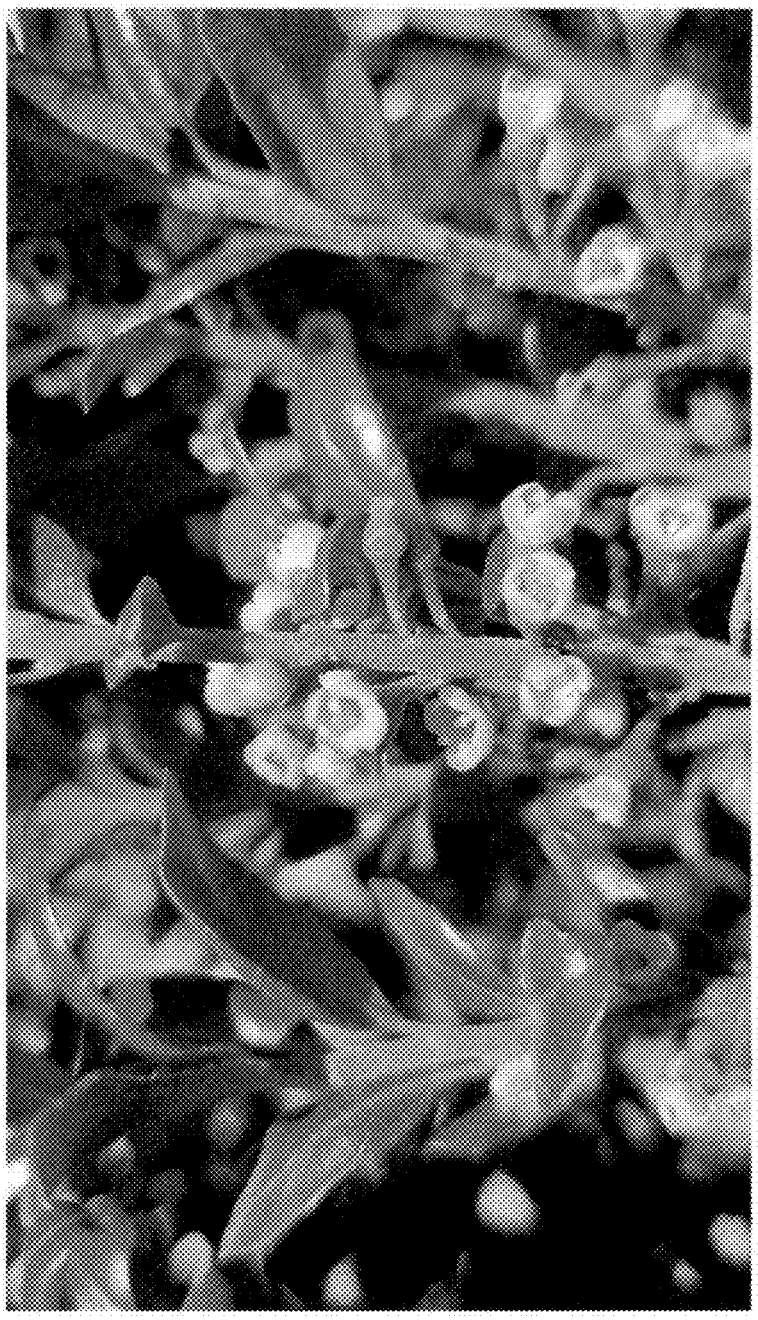
FIG. 3 is a close-up view of typical flowers of the new cultivar. The photographs were taken using conventional techniques and although colors may appear different from actual colors due to light reflectance it is as accurate as possible by conventional photographic techniques.

In the following description, color references are made to The Royal Horticultural Society Colour Chart 2015 except where general terms of ordinary dictionary significance are used. The following observations and measurements describe 'FARROWICUPRT' plants grown May through June of 2024 in a poly-greenhouse in Grand Haven, Michigan. Plants are approximately 3 years old, in 3-gallon containers.

The average day time temperature is 18-27° C., average night temperature is 5-10° C. Measurements and numerical values represent averages of typical plant types.

Botanical classification: *Ilex crenata* 'FARROWICUPRT'.

PROPAGATION

Method: Stem cuttings.

Time to Rooting: 110 days in winter.

Time to Produce Rooted Plant: 140 days in winter.

Root Description: Moderately dense, freely branching, fibrous and fleshy, thin to medium thickness. Tan in color, not accurately measured by the color chart.

PLANT

Plant Type: Evergreen shrub. Fruit producing female *Ilex*.

Plant Shape: Columnar/fastigiate.

Growth Habit: Upwards.

Height: 85 cm.

Plant Spread: 30 cm.

Growth Rate: Moderate.

Plant Vigor: Moderately vigorous.

Branching Characteristics:

*Lateral Branches*.—Branching Habit: Basal; no pinching required. Quantity: 15 to 20. Length: About 52 cm. Diameter: About 4.25 mm.

*Stem*.—Shape: Rounded. Aspect: 70° to 90°. Strength: Strong. Pubescence: None. Color: New Growth: R.H.S. Yellow-Green 146B. Old Growth: R.H.S. Grey-Brown 199B.

*Internode Length*.—5 mm.

FOLIAGE

Leaf:

*Type*.—Single.

*Arrangement*.—Alternate spiral.

*Length*.—2.25 cm.

*Width*.—1 cm.

*Shape*.—Narrowly obovate.

*Apex*.—Broadly acute.

*Base*.—Attenuate.

*Margin*.—Entire, though with some (2 to 4) inconspicuous notches/serrations towards the apex; paired, 1 to 2 per leaf.

*Texture of top surface*.—Glabrous.

*Texture of bottom surface*.—Glabrous.

*Color*.—Young foliage upper side: R.H.S. Yellow-Green 147A. Young foliage under side: R.H.S. Yellow-Green 146B. Mature foliage upper side: R.H.S. Greyed-Green N189A. Mature foliage under side: R.H.S. Yellow-Green 146B.

*Venation*.—Veins indistinguishable from rest of leaf.

Petiole:

*Length*.—3 mm.

*Diameter*.—1 mm.

*Texture, upper side*.—Glabrous.

*Texture, under side*.—Glabrous.

*Color, upper side*.—R.H.S. Greyed-Green N189A.

*Color, under side*.—R.H.S. Yellow-Green 146B.

FLOWER

Bloom Period: Early summer (May-June).

Inflorescence:

*Arrangement*.—Small cymes of 3 flowers in leaf axils of new (seasonal) growth.

*Type or Form*.—Cyme.

*Height*.—6 mm.

*Width*.—1.1 cm.

*Flowers per Inflorescence*.—3.

Flowers:

*Type or Form*.—Whorl.

*Habit*.—In small cymes of 3 flowers in the leaf axils of new (seasonal) growth, concentrated medially on the lateral branches.

*Aspect*.—Outward.

*Quantity of flowers per lateral stem*.—100 to 200.

*Quantity of buds per lateral stem*.—Approximately 20.

*Quantity of flowers and buds per plant*.—About 1,000.

*Length*.—4 mm.

*Diameter*.—4 mm.

*Depth*.—2 mm.

*Persistence*.—Self-cleaning.

*Longevity*.—1 to 2 weeks on plant.

*Fragrance*.—None.

Petals:

*Appearance*.—Diminutive, smooth.

*Arrangement*.—Cruciform.

*Length*.—2 mm.

*Width*.—2 mm.

*Apex*.—Obtuse.

*Base*.—Fused.

*Shape*.—Globose.

*Margin*.—Entire.

*Number*.—4.

*Fused*.—Yes.

*Texture*.—Both sides glabrous and soft.

*Color*.—Upper surface at first opening: R.H.S. Yellow-Green 145C. Under surface at first opening R.H.S. Yellow-Green 145C. Upper surface at maturity: R.H.S. Yellow-Green 145C. Under surface at maturity: R.H.S. Yellow-Green 145C.

Bud:

*Shape*.—Orbicular to ovoid.

*Length*.—2 mm.

*Diameter*.—3 mm.

*Color*.—R.H.S. Yellow-Green 145C.

Sepals: Sepals are indistinguishable from calyx.

Calyx:

*Shape*.—Cup-like.

*Length*.—2 mm.

*Diameter*.—2 mm.

Peduncle:
*Length*.—3 mm.
*Diameter*.—1 mm.
*Color*.—R.H.S. Yellow-Green 144A.
*Texture*.—Glabrous.
*Aspect*.—45°.
*Strength*.—Good.

Pedicels:
*Length*.—3 mm.
*Diameter*.—1 mm.
*Color*.—R.H.S. Yellow-Green 144A.
*Texture*.—Glabrous.
*Aspect*.—45° to 90°.
*Strength*.—Good.

REPRODUCTIVE ORGANS

Stamens: Flower is female.

Pistil:
*Number*.—1.
*Length*.—1 mm.
*Style*.—Length: 1 mm. Color: R.H.S. Yellow-Green 144A. Ovary Color: R.H.S. Yellow-Green 144A.
*Stigma*.—Shape: Peltate. Color: R.H.S. Yellow-Green 144A.

SEED AND FRUIT

Seed:
*Quantity*.—1 to 3 per flower.
*Length*.—3 mm.
*Diameter*.—2 mm.
*Color*.—R.H.S. Brown N200C.

Fruit:
*Type*.—Berry-like drupe.
*Quantity per lateral branch*.—Sparse; fewer than 10.
*Quantity per plant*.—Less than 100.
*Length*.—5 mm.
*Diameter*.—5 mm.
*Color*.—R.H.S. Black 203B.

OTHER CHARACTERISTICS

Disease and Pest Resistance: Neither resistance nor susceptibility to normal pests of *Ilex* observed.

Temperature Tolerance: Tolerant to USDA Zone 5-9.

What is claimed is:

1. A new and distinct cultivar of *Ilex* plant named 'FARROWICUPRT' as herein illustrated and described.

* * * * *